(12) United States Patent
Shen et al.

(10) Patent No.: US 10,548,546 B2
(45) Date of Patent: Feb. 4, 2020

(54) MEDICAL EXAMINATION DEVICE (71) Applicants: BOE TECHNOLOGY GROUP CO., LTD., Beijing (CN); K-tronics (Su Zhou) Technology Co., Ltd., Suzhou, Jiangsu Province (CN)

(72) Inventors: Daliang Shen, Beijing (CN); Weijun Huang, Beijing (CN)

(73) Assignees: BOE TECHNOLOGY GROUP CO., LTD., Beijing (CN); K-TRONICS (SUZHOU) TECHNOLOGY CO., LTD., Suzhou, Jiangsu Province (CN)

( * ) Notice: Subject to any disclaimer, the term of this patent is extended or adjusted under 35 U.S.C. 154(b) by 218 days.

(21) Appl. No.: 15/658,386

(22) Filed: Jul. 24, 2017

(65) Prior Publication Data
US 2018/0055466 A1 Mar. 1, 2018

(30) Foreign Application Priority Data
Aug. 30, 2016 (CN) .......................... 2016 1 0772840

(51) Int. Cl.
*A61B 6/10* (2006.01)
*A61B 6/00* (2006.01)

(52) U.S. Cl.
CPC ............ *A61B 6/4435* (2013.01); *A61B 6/107* (2013.01); *A61B 6/462* (2013.01); *A61B 6/487* (2013.01); *A61B 6/5205* (2013.01)

(58) Field of Classification Search
CPC ........ A61B 6/4435; A61B 6/107; A61B 6/462
See application file for complete search history.

(56) References Cited

U.S. PATENT DOCUMENTS

| 4,472,637 | A | * | 9/1984 | Sportelli | .............. | A61N 5/1042 |
| | | | | | | 250/515.1 |
| 2003/0169847 | A1 | * | 9/2003 | Karellas | ................ | A61B 6/481 |
| | | | | | | 378/98.3 |
| 2009/0213987 | A1 | * | 8/2009 | Stein | ...................... | A61B 6/025 |
| | | | | | | 378/37 |
| 2012/0051520 | A1 | * | 3/2012 | Hoernig | ................ | A61B 6/107 |
| | | | | | | 378/98.5 |

* cited by examiner

*Primary Examiner* — Hugh Maupin
(74) *Attorney, Agent, or Firm* — Kinney & Lange, P.A.

(57) ABSTRACT

A medical examination device is disclosed, which belongs to the technical field of a fluoroscopy examination, comprising: a display configured to display images; an X-ray source configured to transmit an X-ray; an X-ray detector, which is configured to detect the transmitted X-ray which is emitted from the X-ray source and transmitted through an object to be detected, and to output a detection signal; and a control module, which is configured to connect with the X-ray detector so as to receive the detection signal, to generate images based on the detection signal and to transmit the generated images to the display. One of the X-ray source and the X-ray detector is positioned at a back portion of the display.

13 Claims, 4 Drawing Sheets

MEDICAL EXAMINATION DEVICE

CROSS-REFERENCE TO RELATED INVENTION

The present disclosure claims the benefit of Chinese Patent Application Invention No. 201610772840.9 filed on Aug. 30, 2016 in the State Intellectual Property Office of China, the whole disclosure of which is incorporated herein by reference.

BACKGROUND OF THE INVENTION

Field of the Invention

At least one embodiment of the present disclosure relates to the technical field of a fluoroscopy examination, and in particular, to a medical examination device.

Description of the Related Art

An X-ray is usually adapted medically to perform a fluoroscopy examination. Nowadays, upon X-ray examination on a patient in hospital, the examination is usually implemented in a dedicated X-ray Radiation Room and takes a relatively long time.

SUMMARY OF THE INVENTION

At least one embodiment of the present disclosure has been made to overcome or alleviate at least one aspect of the above mentioned disadvantages and/or shortcomings in the prior art, e.g., in order to solve the problem of relatively long time consumption with a dedicated X-ray Radiation Room during an X-ray examination in prior art, by providing a medical examination device according to at least one example of the disclosure.

Following technical solutions are adopted in at least one exemplary embodiment of the invention for achieving the above desired technical purposes.

According to an aspect of at least one exemplary embodiment of the present disclosure, there is provided a medical examination device, comprising: a display configured to display images; an X-ray source configured to transmit an X-ray; an X-ray detector, which is configured to detect the transmitted X-ray which is emitted from the X-ray source and transmitted through an object to be detected, and to output a detection signal; and a control module, which is configured to connect with the X-ray detector so as to receive the detection signal, to generate images based on the detection signal and to transmit the generated images to the display. One of the X-ray source and the X-ray detector is positioned at a back portion of the display.

In at least one embodiment of the disclosure, the medical examination device further comprises an X-ray barrier wall which is also positioned at the back portion of the display, located between the display and both of the X-ray source and the X-ray detector, and provided with a barrier area for the X-ray whose size and shape are adjustable.

In at least one embodiment of the disclosure, the X-ray barrier area comprises: a first rectangular barrier layer having a first thickness; and four second barrier layers, each having a second thickness respectively. The first rectangular barrier layer and the display are of a substantially the same size; the first rectangular barrier layer comprises a first layer and a second layer overlapping and opposite to each other, and four openings each provided at a corresponding one of the four sides thereof, the first layer and the second layer being provided to fit with each other in shape, with a hollow structure provided therebetween, and the four openings being uniformly spaced apart one another and in communication with the hollow structure thereof, respectively; and each of the four second barrier layers is of a single-layered structure, which penetrates from and through the four openings, and is inserted into the hollow structure of the first rectangular barrier layer and provided within the four openings respectively, the four second barrier layers being slidable from the hollow structure of the first rectangular barrier layer towards outside thereof, or slidable from outside of the first rectangular barrier layer towards the hollow structure thereof, through the four openings respectively, so as to adjust both size and shape of the barrier area of the X-ray barrier wall.

In at least one embodiment of the disclosure, the X-ray barrier wall further comprises four spring components each of which is provided between a central position of the hollow structure of the first rectangular barrier layer and a corresponding one of the four second barrier layers, and configured to move the corresponding one second barrier layer outwards relative to the first rectangular barrier layer by a respective elastic force; and the hollow structure of the first rectangular barrier layer is further provided with four bayonet constructions corresponding to the spring components respectively, each of which is configured to get a corresponding second barrier layer stuck, stopped and at least partially locked therein such that the X-ray barrier wall is folded.

In at least one embodiment of the disclosure, the X-ray barrier wall is a cover formed by lead which is concave towards a side of the display.

In at least one embodiment of the disclosure, the X-ray detector is a low-dose X-ray detector; and an X-ray flat-panel detector which is capable of detecting an X-ray ranging between 2-4 mSv/hr functions as the low-dose X-ray detector.

In at least one embodiment of the disclosure, the X-ray source and the X-ray detector are provided opposite to each other, with a threshold distance therebetween larger than a width of an object to be detected.

In at least one embodiment of the disclosure, a rotary mechanism is provided between the X-ray source and the X-ray detector; and the X-ray detector and the X-ray source are connected with each other by the rotary mechanism such that one of the X-ray detector and the X-ray source is rotatable relative to the other thereof, so as to ensure the object to be detected is provided therebetween.

In at least one embodiment of the disclosure, the X-ray source comprises an X-ray tube and a beam limiter which is provided on a light exiting side of the X-ray tube and configured to limit an irradiation range of the X-ray.

In at least one embodiment of the disclosure, the X-ray detector is an X-ray flat-panel detector which comprises X-ray optical inductors and a pixel array which is configured to read out signals and is connected with the control module.

In at least one embodiment of the disclosure, the medical examination device further comprises: a base; a support provided on the base, with the back portion of the display being in turn provided thereon; and a first elevating mechanism. At least one of the X-ray source and the X-ray detector is further provided on and movably connected with the support, and is movable up and down along the support by the first elevating mechanism.

In at least one embodiment of the disclosure, on the support a second elevating mechanism is provided, which is configured to adjust a height of the display, and by which the back portion of the display is provided on the support.

In at least one embodiment of the disclosure, the support is configured to be a hollow one within which the control module is provided.

In at least one embodiment of the disclosure, each of the X-ray detector and the control module comprises a wireless transceiver device through which they are connected with each other wirelessly.

BRIEF DESCRIPTION OF THE DRAWINGS

The above and other features and advantages of the present disclosure will become more apparent and a more comprehensive understanding of the present disclosure can be obtained, by describing in detail exemplary embodiments thereof with reference to the accompanying drawings, in which.

DETAILED DESCRIPTION OF PREFERRED EMBODIMENTS OF THE INVENTION

Exemplary embodiments of the present disclosure will be described hereinafter in detail with reference to the attached drawings, wherein the like reference numerals refer to the like elements. The present disclosure may, however, be embodied in many different forms, and thus the detailed description of the embodiment of the disclosure in view of attached drawings should not be construed as being limited to the embodiment set forth herein; rather, these embodiments are provided so that the present disclosure will be thorough and complete, and will fully convey the general concept of the disclosure to those skilled in the art.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Respective dimension and shape of each component in the drawings are only intended to exemplarily illustrate the contents of the disclosure, rather than to demonstrate the practical dimension or proportion of components of a medical examination device of at least one embodiment of the disclosure.

Figure 1A:
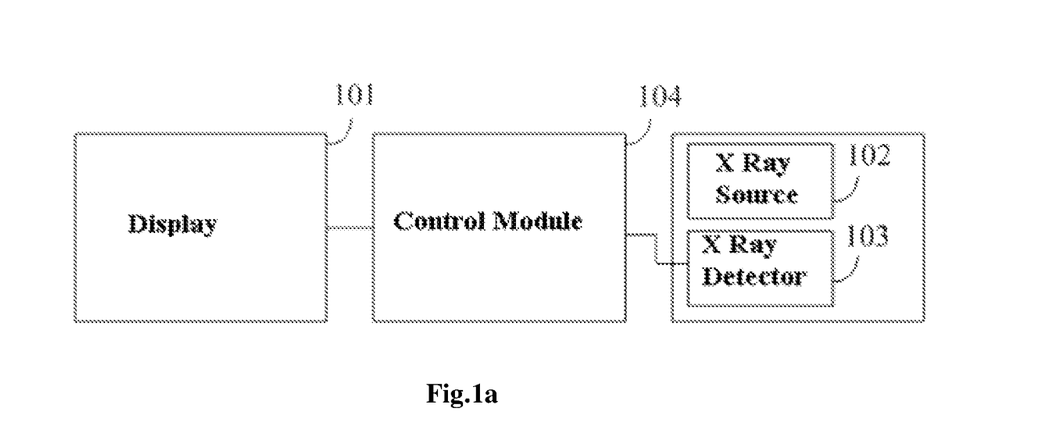
FIG. 1a illustrates a schematic block diagram of a medical examination device according to at least one exemplary embodiment of the disclosure.

According to a general technical concept of at least one embodiment of the present disclosure, as illustrated in FIG. 1a, there is provided a block diagram of a medical examination device, as illustrated in FIG. 1a, comprising:

a display 101 configured to display images;

an X-ray source 102 configured to transmit an X-ray;

an X-ray detector 103, which is configured to detect the transmitted X-ray which is emitted from the X-ray source and transmitted through an object to be detected, and to output a detection signal; and a control module 104, which is configured to connect with the X-ray detector 103 so as to receive the detection signal, to generate images based on the detection signal and to transmit the generated images to the display 101.

Figure 1B:
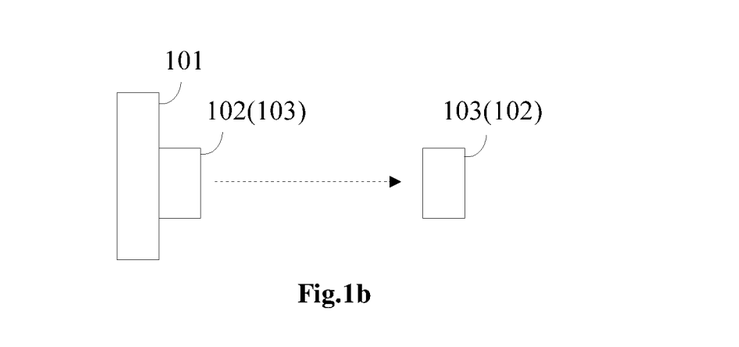
FIG. 1b illustrates a structural schematic side view of the medical examination device according to at least one exemplary embodiment of the disclosure.

FIG. 1b illustrates a structural schematic side view of the medical examination device according to at least one exemplary embodiment of the disclosure. As illustrated in FIG. 1b, one of the X-ray source 102 and the X-ray detector 103 is positioned at a back portion of the display 101.

In the disclosure, the X-ray source or the X-ray detector is integrated with the display into a same device, such that an X-ray irradiates a patient, e.g., by the X-ray source on the medical examination device during a diagnosis and treatment by a doctor, and a result of the irradiation is displayed in real-time on the display, so as to solve the problem of complicated processes of the X-ray irradiation and to save time; besides, this irradiation way may decrease cost for the diagnosis and treatment as compared with a dedicated X-ray Radiation Room. Furthermore, an X-ray detection apparatus and the display are provided integrally, facilitating user's operation thereon.

In order to decrease a radiation of the X-ray, e.g., a low-dose X-ray is used to irradiate. Correspondingly, the X-ray detector 103 is a low-dose X-ray detector; and an X-ray flat-panel detector which is capable of detecting an X-ray ranging between 2-4 mSv/hr functions as the low-dose X-ray detector.

By way of example, the X-ray detector is an X-ray flat-panel detector which comprises X-ray optical inductors and a pixel array which is configured to read out signals and is connected with the control module 104.

Furthermore, by way of example, the X-ray flat-panel detector comprises a data acquisition circuit which is configured to convert an electrical signal outputted by the pixel array into a detection signal, and the pixel array is arranged to electrically connect with the data acquisition circuit. The pixel array is irradiated by the X-ray so as to produce the electrical signal. Since the pixel array is formed by arranging a plurality of units in an array, a signal thus produced may function as various pixel points of an image so as to implement a detection of the X-ray.

The data acquisition circuit is an analog/digital conversion circuit, for example.

Furthermore, a rotary mechanism is provided between the X-ray source 103 and the X-ray detector 102.

Figure 1C:
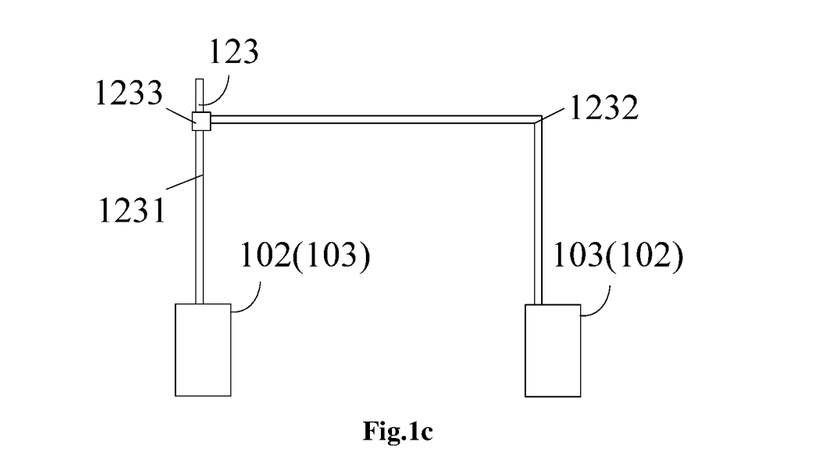
FIG. 1c illustrates a structural schematic view of a rotary mechanism according to at least one exemplary embodiment of the disclosure.

FIG. 1c illustrates a structural schematic view of a rotary mechanism according to at least one exemplary embodiment of the disclosure, as illustrated in FIG. 1c:

In at least one embodiment of the disclosure, when the X-ray source 102 is provided on the back portion of the display 101, the X-ray detector 103 is connected with the X-ray source 102 by a rotary mechanism 123 such that the X-ray detector 103 is rotatable relative to the X-ray source 102, so as to ensure the object to be detected is provided between the X-ray source 102 and the X-ray detector 103.

In an alternative embodiment of the disclosure, when the X-ray detector 103 is provided on the back portion of the display 101, the X-ray source 102 is connected with the X-ray detector 103 by a rotary mechanism 123 such that the X-ray source 102 is rotatable relative to the X-ray detector 103, so as to ensure the object to be detected is provided between the X-ray source 102 and the X-ray detector 103.

As illustrated in FIG. 1c, for example, the rotary mechanism 123 comprises: a vertical shaft 1231, an L-shaped shaft 1232 and a sleeve 1233. An end of the vertical shaft 1231 is connected to the X-ray source 102 or the X-ray detector 103, while the other end of the vertical shaft 1231 is fixed and provided on a structure of the room, e.g., a ceiling thereof, for example. The sleeve 1233 is provided rotatably around the vertical shaft 1231 and is axially located thereon by providing a boss thereon. An end of the L-shaped shaft 1232 is connected with the X-ray detector 103 or the X-ray source 102, while the other end of the L-shaped shaft 1232 is connected to an external wall of the sleeve 1233, with the whole L-shaped shaft 1232 being rotated around the vertical shaft 1231 by the sleeve 1233, so as to implement a functionality thereof.

Figure 2:
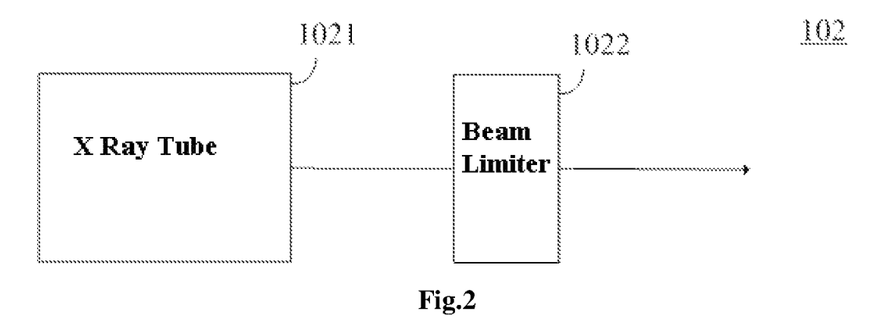
FIG. 2 illustrates a schematic block diagram of an X-ray source according to at least one exemplary embodiment of the disclosure.

FIG. 2 illustrates a schematic block diagram of an X-ray source according to at least one exemplary embodiment of the disclosure. As illustrated in FIG. 2, the X-ray source 102 comprises an X-ray tube 1021 and a beam limiter 1022 which is provided on a light exiting side of the X-ray tube 1021 and configured to limit an irradiation range of the X-ray. The irradiation by the X-ray is implemented, and the irradiation range thereof is restricted by the beam limiter 1022, such that the X-ray irradiates locations on the human body which are to be detected, hereby decreasing the irradiation of the X-ray on the human body.

By way of example, the beam limiter 1022 is a movable beam limiter which is relatively flexible and convenient in both selection and adjustment of the irradiation range during use, so as to meet restrictive requirements of various dimensions at any distance.

Upon implementation, by way of example, the X-ray tube 1021 comprises a package which is a high vacuum glass component and a die which is provided within the package and configured to convert an electric energy into an X-ray. The beam limiter 102 comprises a light limiting plate, a collimating slit and a structural frame. The X-ray is partially occluded after passing through the light limiting plate, and a portion of the X-ray which is transmitted through the light limiting plate is projected onto the collimating slit, so as to further decrease the irradiation range thereof, and finally irradiates on the human body.

Correspondingly, the control module 104 may control a dose of the X-ray which exits the X-ray source 102 by controlling a voltage applied on the X-ray tube 1021, without a repeated more detailed depiction thereof herein.

In at least one embodiment of the disclosure, the X-ray source 102 and the X-ray detector 103 are provided opposite to each other, with a threshold distance therebetween larger than a width of an object to be detected, so as to ensure that the object to be detected is located between the X-ray source 102 and the X-ray detector 103.

Figure 3A:
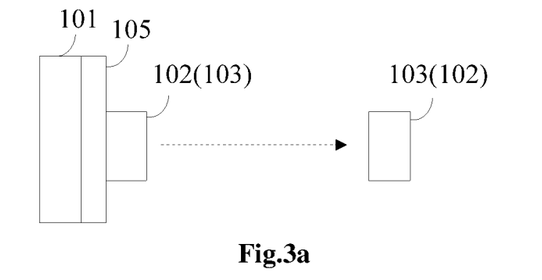
FIG. 3a illustrates a structural schematic side view of another medical examination device according to at least one exemplary embodiment of the disclosure.

FIG. 3a illustrates a structural schematic side view of another medical examination device according to at least one exemplary embodiment of the disclosure. As illustrated in FIG. 3a, as compared with the medical examination device provided in FIG. 1b, the medical examination device illustrated herein further comprises an X-ray barrier wall 105 which is also positioned at the back portion of the display, located between the display 101 and the X-ray source 102, and between the X-ray detector 103 and the display 101. And the radiation of the X-ray may be decreased by increasing the X-ray barrier wall 105.

Figure 3B:
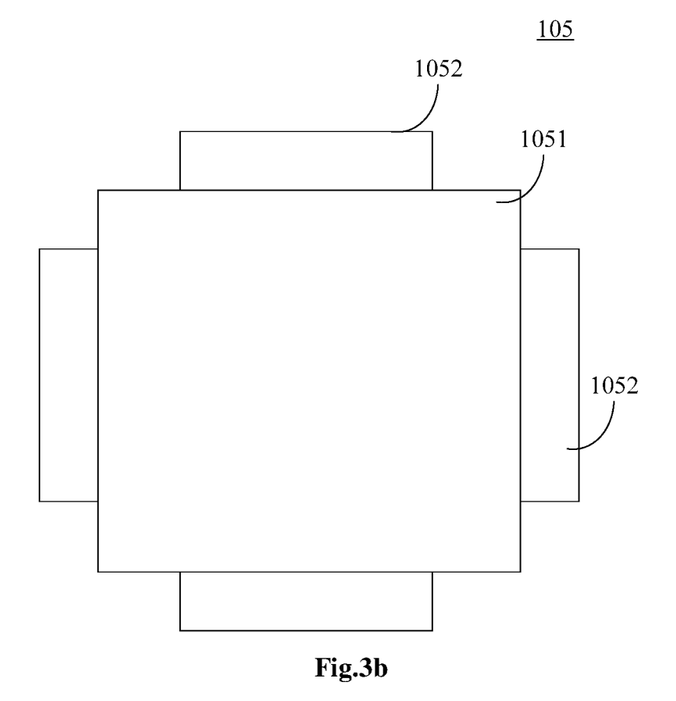
FIG. 3b illustrates a structural schematic sectional view of an X-ray barrier wall according to at least one exemplary embodiment of the disclosure.

As illustrated in FIG. 3b, i.e., a sectional view of FIG. 3a, for example, the X-ray barrier wall 106 comprises: a first rectangular barrier layer 1051 having a first thickness, which is of a size substantially the same as that of the display 101.

Figure 3C:
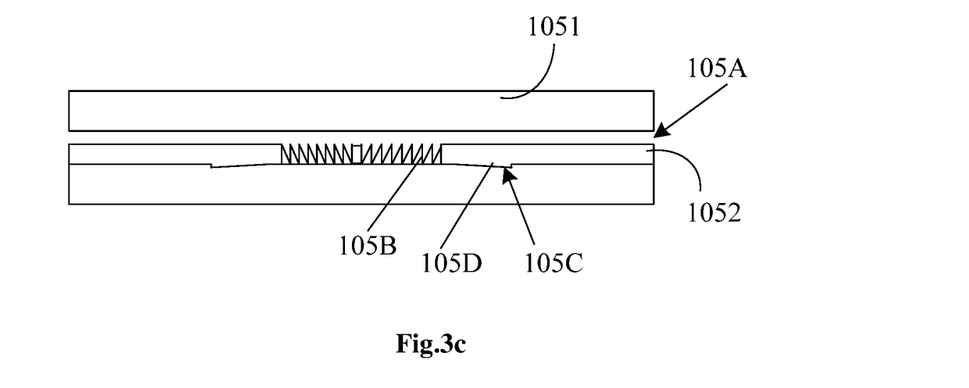
FIG. 3c illustrates a structural schematic side view of the X-ray barrier wall according to at least one exemplary embodiment of the disclosure.

As illustrated in FIG. 3c, the first rectangular barrier layer 1051 comprises a first layer and a second layer overlapping and opposite to each other, and four openings 105A each provided at a corresponding one of the four sides thereof respectively, the first layer and the second layer being provided to fit with each other in shape, with a hollow structure provided therebetween, and the four openings 105A being uniformly spaced apart one another and in communication with the hollow structure thereof, respectively.

The X-ray barrier wall 105 further comprises four second barrier layers 1052, each having a second thickness respectively. Each of the four second barrier layers 1052 is of a single-layered structure, which penetrates from and through the four openings 105A, and is inserted into the hollow structure of the first rectangular barrier layer 1051 respectively, the four second barrier layers being slidable from the hollow structure of the first rectangular barrier layer 1051 towards outside thereof, or slidable from outside of the first rectangular barrier layer 1051 towards the hollow structure thereof, through the four openings 105A respectively, so as to adjust both size and shape of the barrier area of the X-ray barrier wall.

And the first rectangular barrier layer 1051 is of a size substantially the same as that of the display 101 comprises: the first rectangular barrier layer 1051 is sized to be similar to the display, or there is a difference value of respective size between the first rectangular barrier layer 1051 and the display falling within a range, e.g., less than 10% of the size of the display.

By way of example, the first rectangular barrier layer 1051 is a rectangle; and the four openings 105A are strip-shaped openings 105A which are provided respectively on four sides of the first rectangular barrier layers 1051. And for example, the four second barrier layers 1052 are rectangular plates which are shaped to be suitable for inserting into corresponding four openings 105A which are formed to be strip-shaped respectively, such that the four second barrier layers 1052 may extend or retreat within respective openings 105A. The second barrier layers 1052 are each provide with a handle for an operator to grasp, for example.

Furthermore, the X-ray barrier wall 105 further comprises four spring components 105B each of which is provided between a central position of the hollow structure of the first rectangular barrier layer 1051 and a corresponding one of the four second barrier layers 1052, and configured to move the corresponding one second barrier layer 1052 outwards relative to the first rectangular barrier layer 1051 by a respective elastic force.

The hollow structure of the first rectangular barrier layer 1051 is further provided with four bayonet constructions corresponding to the spring components 105B respectively, each of which is configured to get a corresponding second barrier layer 1052 stuck. When the second barrier layers 1052 are pushed inwards by external forces respectively so as to fold the X-ray barrier wall, these second barrier layers 1052 are continuously pushed in until being stopped and stuck at the bayonet constructions.

Figure 3D:
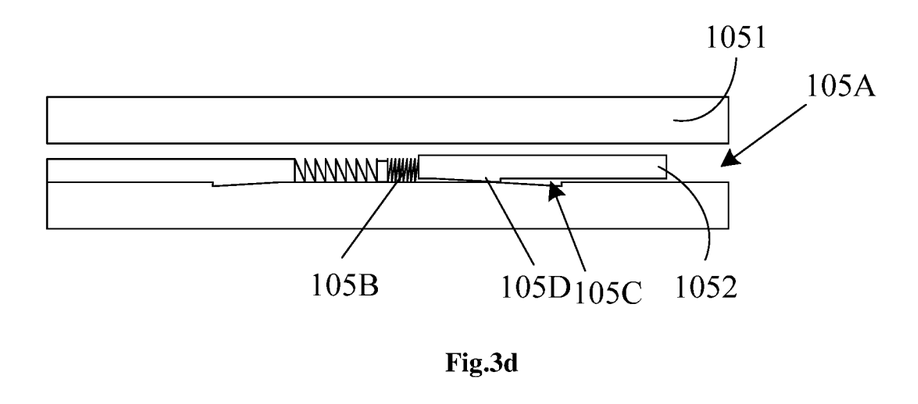
FIG. 3d illustrates a structural schematic view of the X-ray barrier wall according to at least one exemplary embodiment of the disclosure.
Figure 3E:
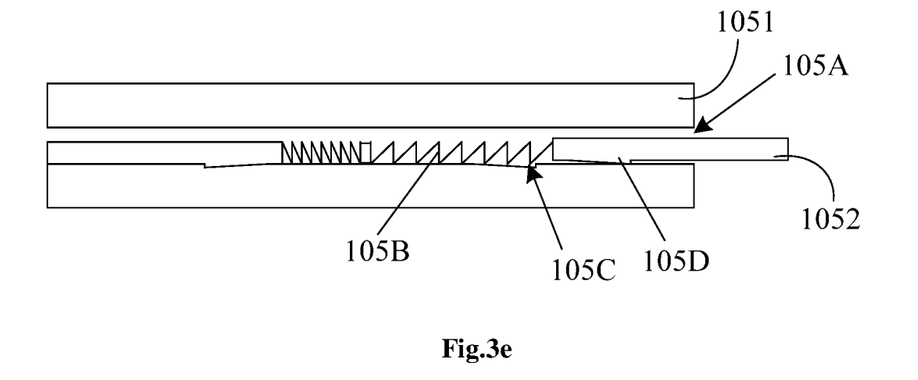
FIG. 3e illustrates a structural schematic view of the X-ray barrier wall according to at least one exemplary embodiment of the disclosure.

By way of example, each of above bayonet constructions is a clamping slot 105C. Correspondingly, each of the second barrier layers 1052 is provided with a protrusion 105D which fits with the corresponding clamping slot 105C, when each of the second barrier layers 1052 is pushed inwards by an external force, the protrusion 105D can be stuck into the corresponding clamping slot 105C such that the X-ray barrier wall is folded. When the second barrier layers 1052 are required to be stretched out, they may be pushed inwards by external forces such that the protrusions 105D may slide out of the corresponding clamping slots 105C so as to be released respectively, as illustrated in FIG. 3*d*. At that time, the operator may apply on each of the second barrier layers 1052 an action force in a direction away from a corresponding one of the clamping slots 105C, e.g., in a direction extending from the hollow structure towards the respective opening 105A, outwards and slightly upwards away from the corresponding clamping slot 105C, such that the second barrier layer 1052 may be pushed to stretch out of the corresponding opening 105A under the action of the corresponding spring component 105B, as illustrated in FIG. 3*e*.

In at least one another embodiment of the disclosure, by way of example, the X-ray barrier wall 105 is a cover formed by lead which is concave towards a side of the display.

Figure 4A:
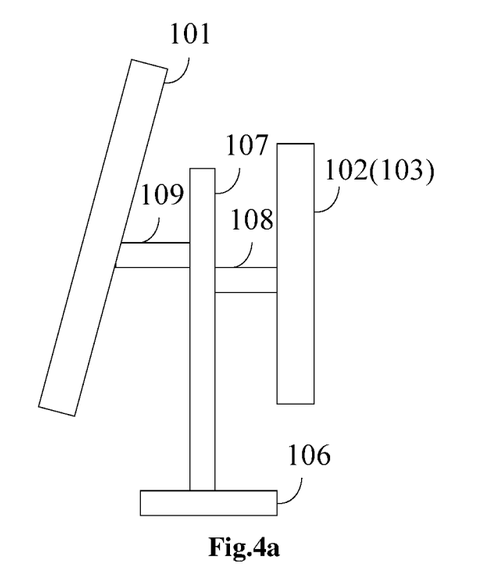
FIG. 4a illustrates a structural schematic view of a base and a support of the medical examination device according to at least one exemplary embodiment of the disclosure.
Figure 4B:
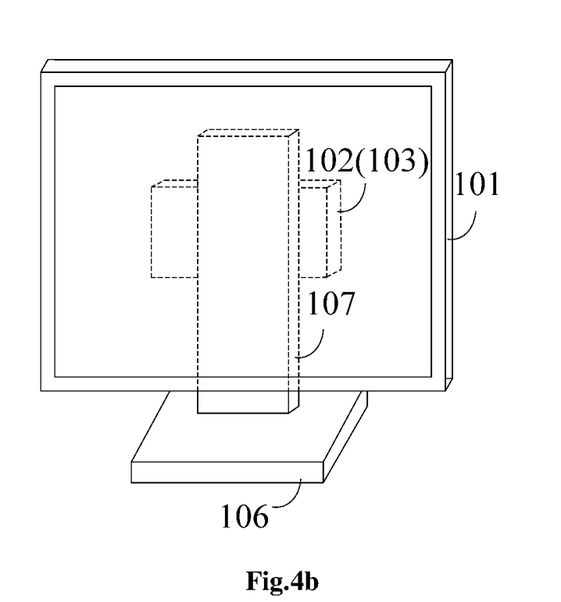
FIG. 4b illustrates a structural schematic view of the base and the support of the medical examination device according to at least one exemplary embodiment of the disclosure.

As illustrated in FIGS. 4*a* and 4*b*, the medical examination device further comprises a base 106; a support 107 provided on the base, with the back portion of the display 101 being in turn provided thereon; and a first elevating mechanism 108. At least one of the X-ray source and the X-ray detector is further provided on and movably connected with the support 107, and is movable up and down along the support 107 by the first elevating mechanism 108, so as to adjust a correspondence relationship between the object to be detected and both of the X-ray source and the X-ray detector. Depending on a height of the patient, the heights of the X-ray source and the X-ray detector are adjustable so as to facilitate use by the operator.

Moreover, on the support 107 a second elevating mechanism 109 is provided, which is configured to adjust a height of the display, and by which the back portion of the display is provided on the support 107. Depending on the height of the operator, typically a doctor or a nurse, the height of the display is adjusted so as to facilitate use by the operator.

As illustrated in FIGS. 4*a* and 4*b*, for example, the base 106 is a rectangular base; while in other embodiments, the base 106 may for example be of other shapes, e.g., a round base and the like.

In addition, the base 106 is for example formed by metal, plastics, or other materials.

As illustrated in FIGS. 4*a* and 4*b*, the support 107 may be of a square pillar shape; however, in other embodiments, the support 107 may be of other shapes, e.g., a cylindrical support and the like.

In addition, the support 107 is for example formed by metal, plastics, or other materials.

Upon implementation, each of the first elevating mechanism 108 and the second elevating mechanism 109 is an elevating mechanism of a pinion-and-rack type.

In at least one embodiment of the disclosure, the elevating mechanism of the pinion-and-rack type comprises a rack provided on the support 107, an elevating pinion provided on the X-ray source 102 or the display 101, and an actuating mechanism which drives the elevating pinion to rise and fall, the rack and the elevating pinion engaging with each other. In at least one embodiment of the disclosure, the actuating mechanism for example comprises a gearbox and a motor which drives the elevating pinion in motion by the gearbox; in another alternative embodiment, the actuating mechanism is for example a manual handle which is connected with a side of the elevating pinion so as to drive the latter in motion.

In at least one embodiment of the disclosure, the support 107 is configured to be a hollow one within which the control module 104 is provided. The control module may be protected by providing it within the support.

Upon implementation, the support 107 is for example formed by a high strength nano material such that the support 107 has a relative high strength and relative light self-weight. An outer contour of the support 107 comprises, but limited to, rectangle, cylinder, and the like.

In at least one embodiment of the disclosure, each of the X-ray detector 103 and the control module 104 comprises a wireless transceiver device through which they are connected with each other wirelessly. The X-ray detector 103 and the control module 104 are connected with each other by a wireless connection, so as to reduce wirings and to facilitate an adjustment of a space between the X-ray detector 103 and the X-ray source 102.

The wireless transceiver comprises, but not limited to, a wireless fidelity module and a Bluetooth module and the like.

In at least one embodiment of the disclosure, the display 101 comprises, but not limited to, a liquid crystal display or an OLED (Organic Light Emitting Diode) display. By way of example, the liquid crystal display or the OLED display may be adopted as the display, which is easily implemented with a superior display effect.

In at least one embodiment of the disclosure, the control module 104 for example comprises a microprocessor. The microprocessor may be adopted as the control module, which is easily implemented with a relatively small volume.

Advantageous technical effects brought about by the technical solutions provided by the embodiment of the disclosure are listed as follows:

In the disclosure, the X-ray source or the X-ray detector is integrated with the display into a same device, such that an X-ray irradiates a patient, e.g., by the X-ray source on the medical examination device during a diagnosis and treatment by a doctor, and a result of the irradiation is displayed in real-time on the display, so as to solve the problem of complicated processes of the X-ray irradiation and to save time; besides, this irradiation way may decrease cost for the diagnosis and treatment as compared with a dedicated X-ray Radiation Room. Furthermore, an X-ray detection apparatus and the display are provided integrally, facilitating user's operation thereon.

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle.

Although the disclosure is described in view of the attached drawings, the embodiments disclosed in the drawings are only intended to illustrate the preferable embodiment of the present disclosure exemplarily, and should not be deemed as a restriction thereof.

Although several exemplary embodiments of the general concept of the present disclosure have been shown and described, it would be appreciated by those skilled in the art that various changes or modifications may be made in these embodiments without departing from the principles and spirit of the disclosure and lie within the scope of present application, which scope is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A medical examination device, comprising:
    a display configured to display images;
    an X-ray source configured to transmit an X-ray;
    an X-ray detector, which is configured to detect the transmitted X-ray which is emitted from the X-ray source and transmitted through an object to be detected, and to output a detection signal; and
    a control module, which is configured to connect with the X-ray detector so as to receive the detection signal, to generate images based on the detection signal and to transmit the generated images to the display,
    wherein one of the X-ray source and the X-ray detector is positioned at a back portion of the display;
    wherein the medical examination device further comprises an X-ray barrier wall which is also positioned at the back portion of the display, located between the display and both of the X-ray source and the X-ray detector, and provided with a barrier area for the X-ray whose size and shape are adjustable; and
    wherein the X-ray barrier wall comprises a first rectangular barrier layer, the first rectangular barrier layer comprises a first layer and a second layer overlapping and opposite to each other, and four openings each provided at a corresponding one of the four sides thereof respectively, the first layer and the second layer being provided to fit with each other in shape, with a hollow structure provided therebetween, and the four openings being uniformly spaced apart one another and in communication with the hollow structure thereof, respectively.

2. The medical examination device according to claim 1, wherein the X-ray barrier wall further comprises:
    four second barrier layers, each having a second thickness respectively,
    wherein the first rectangular barrier layer has a first thickness, the first rectangular barrier layer and the display are of substantially the same size; and
    wherein each of the four second barrier layers is of a single-layered structure, which penetrates from and through the four openings, and is inserted into the hollow structure of the first rectangular barrier layer and provided within the four openings respectively, the four second barrier layers being slidable from the hollow structure of the first rectangular barrier layer towards outside thereof, or slidable from outside of the first rectangular barrier layer towards the hollow structure thereof, through the four openings respectively, so as to adjust both size and shape of the barrier area of the X-ray barrier wall.

3. The medical examination device according to claim 2, wherein the X-ray barrier wall further comprises four spring components each of which is provided between a central position of the hollow structure of the first rectangular barrier layer and a corresponding one of the four second barrier layers, and configured to move the corresponding one second barrier layer outwards relative to the first rectangular barrier layer by a respective elastic force; and
    wherein the hollow structure of the first rectangular barrier layer is further provided with four bayonet constructions corresponding to the spring components respectively, each of which is configured to get a corresponding second barrier layer stuck, stopped and at least partially locked therein such that the X-ray barrier wall is folded.

4. The medical examination device according to claim 1, wherein the X-ray barrier wall is a cover formed by lead which is concave towards a side of the display.

5. The medical examination device according to claim 1, wherein the X-ray detector is a low-dose X-ray detector; and
    wherein an X-ray flat-panel detector which is capable of detecting an X-ray ranging between 2-4 mSv/hr functions as the low-dose X-ray detector.

6. The medical examination device according to claim 1, wherein the X-ray source and the X-ray detector are provided opposite to each other, with a threshold distance therebetween larger than a width of the object to be detected.

7. The medical examination device according to claim 1, wherein a rotary mechanism is provided between the X-ray source and the X-ray detector; and
    wherein the X-ray detector and the X-ray source are connected with each other by the rotary mechanism such that one of the X-ray detector and the X-ray source is rotatable relative to the other thereof, so as to ensure the object to be detected is provided therebetween.

8. The medical examination device according to claim 1, wherein the X-ray source comprises an X-ray tube and a beam limiter which is provided on a light exiting side of the X-ray tube and configured to limit an irradiation range of the X-ray.

9. The medical examination device according to claim 1, wherein the X-ray detector is an X-ray flat-panel detector which comprises X-ray optical inductors and a pixel array which is configured to read out signals and is connected with the control module.

10. The medical examination device according to claim 1, further comprising:
    a base;
    a support provided on the base, with the back portion of the display being in turn provided thereon; and
    a first elevating mechanism,
    wherein at least one of the X-ray source and the X-ray detector is further provided on and movably connected with the support, and is movable up and down along the support by the first elevating mechanism.

11. The medical examination device according to claim 10, wherein on the support a second elevating mechanism is provided, which is configured to adjust a height of the display, and by which the back portion of the display is provided on the support.

12. The medical examination device according to claim 10, wherein the support is configured to be a hollow support within which the control module is provided.

13. The medical examination device according to claim 1, wherein each of the X-ray detector and the control module comprises a wireless transceiver device through which they are connected with each other wirelessly.

* * * * *